United States Patent [19]

Ellis et al.

[11] Patent Number: 4,645,932

[45] Date of Patent: Feb. 24, 1987

[54] DIODES WITH CHEMICALLY SENSITIVE LUMINESCENCE

[75] Inventors: Arthur B. Ellis, Madison, Wis.; Michael K. Carpenter, Warren, Mich.

[73] Assignee: Minnesota Mining and Manufacturing Company, St. Paul, Minn.

[21] Appl. No.: 712,799

[22] Filed: Mar. 18, 1985

[51] Int. Cl.$^4$ ............................................. G01N 27/12
[52] U.S. Cl. .................................... 250/361 R; 73/23; 250/370
[58] Field of Search ............... 250/361 R, 362, 370 K; 252/301.4 S; 73/23; 422/88

[56] References Cited

U.S. PATENT DOCUMENTS 4,058,368 11/1977 Svensson et al. ...................... 73/23
4,211,586 7/1980 Fang et al. ............................ 148/175
4,542,640 9/1985 Clifford .................................. 73/23

OTHER PUBLICATIONS

Carpenter et al, "Photoluminescent Response of Palladium . . . [Coated] Diodes to $H_2$", Langmuir, 1985, 1, 605–607.
Imai, H. et al, "Catastrophic Degradation of GaAlAS DH Laser Diodes", Appl. Phys. Lett. 33(12), 15 Dec. 1978.

*Primary Examiner*—Carolyn E. Fields
*Assistant Examiner*—Richard Hanig
*Attorney, Agent, or Firm*—Donald M. Sell; James A. Smith; Mark A. Litman

[57] ABSTRACT

The presence of certain chemicals on the emitting surface of the palladium coated photoluminescent semiconductor alters the characteristics of radiation emitted from said surface. This alteration is used to indicate the presence of those chemicals in the environment.

20 Claims, No Drawings

DIODES WITH CHEMICALLY SENSITIVE LUMINESCENCE

TECHNICAL FIELD

The present invention relates to optically coupled chemical sensing devices and to processes for detecting the presence of certain classes of chemical compounds.

BACKGROUND OF THE ART

Electroluminescence occurs in semiconductor materials which are capable of emitting visible or near visible radiation when an electrical current passes through the semiconductor. Photoluminescence can also occur in these materials. If external light is used to excite the semiconductor, a characteristic wavelength of light is emitted. These characteristic wavelengths vary amongst different photoluminescent semiconductors and can be varied in a single semiconductor by doping the material. The dopant will ordinarily cause a shift in the wavelength of radiation emitted by the material.

Amongst the various studies on the luminescence of photo-stimulated or electroluminescent materials is "Luminescent Photoelectrochemical Cells", Streckert, H. H., Tong, J. and Ellis, A. B., J. Am. Chem. Soc., Vol. 104, No. 2, 1982, pp. 581–588. It is noted therein that the intensity of light emitted by electroluminescence and photoluminescence varies directly with the applied voltage. The efficiency of charge transfer and good electrical contact at the surface is also noted as important in the efficiency of the process.

U.S. patent application Ser. No. 480,471 filed on Mar. 30, 1983 discloses semiconductor electrodes having multicolor luminescence. These semiconductors comprise solid state solutions of three elements which vary in a vertically anisotropic manner. The preferred solid state solutions are of cadmium, sulfur and selenium.

U.S. Pat. No. 4,211,586 discloses a method of forming a multicolor light-emitting array of diodes. The diodes are formed by differentially etching a graded n-type semiconductor and diffusing a p-type dopant into the surface of the n-type semiconductor to form a p-n junction diode.

SUMMARY OF THE INVENTION

It has been found in the practice of the present invention that palladium coated photoluminescent semiconductors exhibit an optical response to certain compounds during photostimulation. Compounds which dissociate on contact with metals to provide atomic or molecular hydrogen sufficiently perturb the photoluminescent intensity or spectral distribution of Pd containing Schottky diodes so that mechanical or visual detection of that perturbation can be made.

DETAILED DESCRIPTION OF THE INVENTION

Photoluminescent Schottky diodes with barriers resulting from transparent or translucent palladium and other metal coatings with n-type or p-type semiconductors exhibit alterations in their photoluminescent properties when exposed to certain compounds. It is believed that compounds which liberate or form atomic or molecular hydrogen on contact with palladium or other metals (such as platinum, rhodium, etc.) affect the metal work function in the diode. This effect can be sensitive to parts per million of such compounds in the environment.

Schottky barriers are formed by a metal-to-semiconductor interface which exhibits a non-linear impedance. The (Schottky) barrier arises because of the contact potential (difference in work functions) between the metal and the semiconductor. The "diffusional potential" or "bandbending" $V_{d0}$ should be equal to the difference between the work functions $(\phi_m - \phi_s)$, and the barrier height $\phi_b$ seen from the metal should consequently be given by the difference between the metal work function $\phi_m$ and the electron affinity of the semiconductor $\chi_s$. (Metal-semiconductor Contacts, E. H. Rhoderick, Clarendon Press, Oxford, 1978, p. 3.)

Photoluminescent semiconductors are well known in the art. They are generally solid state solutions of at least two or three elements which, when stimulated by actinic radiation, emit radiation. Both the actinic and emitted radiation are generally visible or near visible radiation (300–900 nm). When a coating over the radiation emitting surface of the semiconductor is a metal (such as palladium) which when penetrated by hydrogen alters the height of the Schottky barrier, the luminescence of the semiconductor has been found to be altered by the presence of atomic or molecular hydrogen on the radiation emitting surface. Since compounds such as ammonia and hydrazine generate hydrogen when in contact with palladium, variations in photoluminescence are an indication of the presence of such compounds.

Particularly useful n-type semiconductors which can be used to form the detectors according to the present invention are CdS, CdSe, and $CdS_xSe_{1-x}(0 \leq x \leq 1)$. Other useful semiconductors would be ZnSe:Al, $Cd_xZn_{1-x}S(0 \leq x \leq 1)$, $ZnS_xSe_{1-x}(0 \leq x \leq 1)$, $Cd_xZn_{1-x}Se(0 \leq x \leq 1)$, and the like. The palladium can be deposited on the elements according to standard semiconductor manufacturing techniques.

A functional apparatus for actually using this phenomenon for detecting the presence of compounds that release hydrogen in contact with palladium would have at least the following 3 components: the metal coated semiconductor, a source of actinic radiation directed at the radiation emitting surface of the diode formed by the coating on the semiconductor, and an optical detector. The diode has already been described. The actinic radiation source may be merely an opening exposing the diode to available light (room light, sunlight, etc.) or may be any internal source of radiation such as a light bulb, light emitting diode, or laser. The radiometer may be selected from amongst the many commercially available radiometers, its selection being primarily dependent upon the ultimate sensitivity desired in the final article. Fiber optics may be used to carry actinic radiation to the diode or to carry emitted radiation away from the diode.

The distribution of hydrogen on the radiation emitting surface of the semiconductor is in a state of equilibrium. The equilibrium is generally reached in a matter of seconds. Between uses, storage in an environment free of hydrogen-releasing compounds or in normal room conditions, will be sufficient to clean the semiconductor surface. It is generally best to equilibrate the detector in an environment which is similar to that in which a change in the concentration of hydrogen-releasing gas might be expected. The latter will enable the detection of a change in the concentration of hydrogen-releasing compounds in the environment while the former would register residuals of such compounds also.

The metal layer in the photoconductor should be between 10 and 750 Angstroms, preferably between 20 and 500 Angstroms, more preferably between 30 and 400 Angstroms.

EXAMPLE

Samples of n-type, single-crystal, CdS and CdSe c-plates (1-mm thickness; ~2 ohm-cm resistivity) were obtained commercially and cut into pieces of 0.25-cm$^2$ area. "C-plate" indicates that in the particular sample, the face of the crystal onto which the metal is being deposited is perpendicular to the c crystallographic axis. Graded samples of n-CdS$_x$Se$_{1-x}$ (0≦x≦1) where the graded zone had a thickness of ~1.0 micrometers were prepared by vapor-phase diffusion of S into CdSe and characterized as described in Carpenter, M. K.; Streckert, H. H.; Ellis, A. B. *J. Solid State Chem.* 1982, 45, 51. Prior to Pd deposition on its 0001 Cd-rich face, the CdS was etched in Br$_2$/MeOH (1:10 v/v); the graded CdS$_x$Se$_{1-x}$ samples were not etched owing to the thinness of the graded layer.

Deposition used Pd foil (50×50×0.1 mm; >99.997% metallic purity) and a commercial sputtering apparatus. Sputtering was conducted at 2×10$^{-4}$ torr Ar pressure and 60-μA beam current for approximately 45 seconds; a parallel deposition onto Pt foil was used in conjunction with electrochemical stripping (0.75 V vs. standard calomel electrode in 1M HCl aqueous electrolyte), estimating the Pd layer thickness as about 100 Å.

Photoluminescent spectra were recorded using 457.9- and 488.0-nm excitation from an argon ion laser. An Aminco-Bowman spectrometer equipped with a Hamamatsu R446S PMT was used to measure variations in emission. The sample was enclosed in a cell which permitted dry N$_2$, a 3:1 N$_2$:H$_2$ mixture, or air to bathe the sample; flow rates of approximately 0.5 liters/min were employed.

The photoluminescent spectrum from the Pd-CdS sample in air, illuminated through the metal with 457.9-nm ultraband gap (E$_g$~2.4 eV) light, was characterized by band edge emission at ~510 nm. When a 3:1 mixture of N$_2$:H$_2$ was passed over the sample, the photoluminescent intensity was enhanced by approximately 70%; the enhancement occurred over ~30 s with the 100-Å thick Pd layer. After flushing the sample cell with N$_2$ and then with air, the photoluminescent intensity returned to its original value. This effect was reversible over at least 10 cycles. When more penetrating 488.0-nm light was used for excitation, the photoluminescent intensity was augmented by ~40% with exposure to H$_2$. From current-voltage data, the Pd-CdS structure exhibited typical diode behavior in air and in the N$_2$/H$_2$ medium.

These spectral changes are consistent with a reduction in Schottky barrier height resulting from the dissolution of H$_2$ in Pd. Qualitatively, the photoluminescent intensity is expected to rise because the smaller electric field in the semiconductor allows a larger fraction of e$^-$-h$^+$ pairs to radiatively recombine. By regarding the region supporting the electric field as being completely nonemissive, i.e., a dead-layer, a quantitative expression for relative PL intensity can be obtained, eq. (1):

$$\phi_{air}/\phi_{H_2} = \exp(-\alpha' \Delta D) \quad (1)$$

In this expression, $\phi_{H_2}$ and $\phi_{air}$ are the radiative quantum yields in H$_2$ and in air; ΔD is the difference in dead-layer thickness between the two media; and $\alpha' = (\alpha + \beta)$ with α and β the solid's absorptivities for the exciting and emited light, respectively. For CdS, α is 6×10$^4$ and estimated to be (9–10)×10$^4$ cm$^{-1}$ for 488.0- and 457.9-nm light, respectively, for $\underline{E} \perp \underline{c}$ polarization; β is 7×10$^3$ cm$^{-1}$ at 510 nm.

The photoluminescent enhancements seen for the two excitation wavelengths employed give a consistent value for ΔD of 500–600 Å. This contraction of the electric field upon exposure to H$_2$ can be related to a reduction in Schottky barrier height if the initial height is known. Literature estimates for the Pd-CdS barrier height in air range from ~0.5–0.8 eV. The resultant i-V curves yield an estimated height of 0.6 eV. The depletion width W is related to barrier height qV by eq. (2), $$W = \sqrt{\frac{2\epsilon\epsilon_o V}{qN_D}} \quad (2)$$

where $\epsilon_o$ is the permittivity of free space, q is the electronic charge, and $\epsilon$ and $N_D$ are the semiconductor's dielectric constant and charge carrier density; for our samples, $\epsilon$ and $N_D$ are ~10 and 9×10$^{15}$ cm$^{-3}$, respectively. Substitution into eq. (2), equating D with W, leads to an estimated decline in barrier height of 0.2 eV. Literature values vary from ~0.5 eV to ~0.2 eV (extrapolated). The differences likely reflect variation in sample preparation.

Another illustration of these effects is provided by a Schottky diode formed from a graded CdS$_x$Se$_{1-x}$ sample coated with palladium (Pd-CdS$_x$Se$_{1-x}$). The photoluminescence spectrum in air consists of edge emission from all of the CdS$_x$Se$_{1-x}$ compositions which comprise the graded zone, from CdS at the surface to the CdSe (E$_g$~1.7 eV; λ$_{max}$~720 nm) substrate. A linear correlation exists between composition x and the emission band maximum, eq. (3). In conjunction with AES-/Ar$^+$ (Auger electron spectroscopy/Argon ion) sputter etch data, eq. (3) provides $$\lambda_{max}(nm) = 718 - 210\chi \quad (3)$$

a map of radiative recombination in the solid: The photoluminescence is color-coded to indicate the depth from the surface at which e$^-$-h$^+$ pair recombination occurs. Perturbation of photoluminescence by applied potential reflects changes in the effective electric field (EEF) in the solid. The term "EEF" is used to reflect the fact that the electric field of this solid is complex and contains contributions, e.g., from band edge gradients in addition to the field arising from the Schottky barrier.

Exposure of a Pd-CdS$_x$Se$_{1-x}$ diode to H$_2$ resulted in asymmetric enhancement of as much as 50% in the blue end of the PL spectrum. The effect corresponded to a modest color change. The material had diode i-V characteristics in both environments. Qualitatively, the PL enhancement at shorter wavelengths indicated a reduction in the EEF in the near-surface region of the semiconductor, since it was the S-rich compositions which gave rise to the emission. A more quantitative estimate of the affected region was afforded by the cessation of spectral changes for λ≧600 nm. From eq. (3) and AES-/Ar$^+$ sputter etch data, exposure to H$_2$ influenced the EEF to a depth of ~0.1 micrometers (1000 Å) from the surface.

In summary, bulk PL from Pd-CdS and Pd-CdS$_x$Se$_{1-x}$ Schottky diodes provided a sensitive probe of changes in the electric field of the semiconductors resulting from a surface interaction with H$_2$. The ability to transform molecular surface interactions into a change in bulk PL intensity (Pd-CdS) or color (Pd-CdS$_x$Se$_{1-x}$) clearly has applications to the design of optically-coupled chemical sensors.

We claim:

1. An apparatus for detecting the presence of chemical compounds comprising
    (1) a photoluminescent semiconductor having a metal coating on a radiation emitting surface of said semiconductor, the height of the Schottky barrier of the diode varying when hydrogen is absorbed into the metal layer,
    (2) a source of actinic radiation which can impinge on said radiation emitting surface of the semiconductor, and
    (3) a means for detecting changes in the characteristics of the radiation emitted from said radiation emitting surface.

2. The apparatus of claim 1 wherein said semiconductor having a coating of metal comprises a solid state solution of at least two elements selected from the group of two or three elements consisting of (a) cadmium, selenium and sulfur, (b) zinc, selenium, and sulfur, (c) cadmium, zinc, and selenium, (d) cadmium, zinc and sulfur, (e) cadmium and selenium, (f) cadmium and sulfur, and (g) zinc and selenium doped with aluminum.

3. The apparatus of claim 1 wherein said means for detecting changes in the characteristics of the radiation is a radiometer.

4. The apparatus of claim 2 wherein said means for detecting changes in the characteristics of the radiation is a radiometer.

5. The apparatus of claim 2 wherein said semiconductor has palladium as said metal coating and said semiconductor comprises graded CdSe$_x$S$_{1-x}$ wherein $0 \leq x \leq 1$.

6. The apparatus of claim 3 wherein said semiconductor has palladium as said metal coating and said semiconductor comprises graded CdSe$_x$S$_{1-x}$ wherein $0 \leq x \leq 1$.

7. The apparatus of claim 1 wherein said source of radiation comprises ambient light.

8. The apparatus of claim 3 wherein said source of radiation comprises ambient light.

9. The apparatus of claim 6 wherein said source of radiation comprises ambient light.

10. The apparatus of claim 1 wherein said metal is palladium.

11. The apparatus of claim 2 wherein said metal is palladium.

12. The apparatus of claim 7 wherein said metal is palladium.

13. A process for detecting the presence of chemical components comprising a photoluminescent semiconductor having at least one surface coated with a thin layer of metal, irradiating said surface with actinic radiation, observing the characteristics of radiation emitted from said surface, then exposing said surface to an environment having chemical compounds thereon and detecting any changes in the characteristics of radiation emitted from said surface.

14. The process of claim 13 wherein said actinic radiation is ambient light.

15. The process of claim 13 wherein light from a bulb, laser or light emitting diode impinges on said surface to provide actinic radiation.

16. The process of claim 13 wherein a compound which generates atomic or molecular hydrogen contacts said surface and changes the characteristics of radiation emitted from said surface.

17. The process of claim 14 wherein a compound which generates atomic or molecular hydrogen contacts said surface and changes the characteristics of radiation emitted from said surface.

18. The process of claim 16 wherein a compound which generates atomic or molecular hydrogen contacts said surface and changes the characteristics of radiation emitted from said surface.

19. The process of claim 13 wherein said metal is palladium.

20. The process of claim 15 wherein said metal is palladium.

* * * * *